United States Patent [19]

Burrell, Jr. et al.

[11] 4,357,937

[45] Nov. 9, 1982

[54] MEDICAL IRRIGATION DEVICE

[76] Inventors: Lawrence M. Burrell, Jr., 2702 Briargrove, Houston, Tex. 77057; Jean Cukier, 7000 Fannin, Suite 2400, Houston, Tex. 77030

[21] Appl. No.: 277,658

[22] Filed: Jun. 26, 1981

[51] Int. Cl.³ .............................................. A61M 1/00
[52] U.S. Cl. .................................. 128/232; 128/248
[58] Field of Search ............. 128/227, 224, 230, 232, 128/231, 66, 234, 239, 248, 249, 250, 251

[56] References Cited

U.S. PATENT DOCUMENTS

| | | | |
|---|---|---|---|
| 788,176 | 4/1905 | Traves | 128/227 |
| 1,494,985 | 5/1924 | Beck | 128/231 |
| 3,496,933 | 2/1970 | Lloyd | 128/230 X |
| 3,892,226 | 7/1975 | Rosen | 128/231 X |

*Primary Examiner*—John D. Yasko
*Attorney, Agent, or Firm*—Vaden, Eickenroht, Thompson, Bednar & Jamison

[57] ABSTRACT

A disposable medical irrigation device, manually operated, adapted for providing selective volume and stream intensity in liquid flow from a plurality of syringes. The device has a transparent reservoir vessel mounted upon a base which can rest upon a flat mounting surface and is resistant to tipping even when empty of liquid. The vessel provides liquid to flexible hoses that interconnect with syringes which are arranged to be hand held for ready aiming and directing of a stream of liquid from a nozzle onto a wound or the like for removing blood or other materials, including injury debris such as particles of clothing and the like. The syringes carry unique valve mechanisms so that a light pressure upon a squeeze bulb carried on a syringe initiates a liquid stream from the nozzle but the syringe can rest dribble free between uses. The device is arranged for readily assembly from easy-to-fabricate parts, and it can be sterilized and kept within a film pack until it is needed.

10 Claims, 8 Drawing Figures

MEDICAL IRRIGATION DEVICE

BACKGROUND OF THE INVENTION

1. Field of the Invention

This invention relates to the field of surgery, and more particularly, it relates to apparatus or devices used for irrigating wounds and the like in medical procedures.

2. Description of Prior Art

It is necessary at times during the performance of surgery by medical professionals for wounds to be cleaned of accumulated blood and foreign debris such as particles of clothing, dirt and other undesired materials. The cleaning of these wounds has been accomplished through the use of irrigating devices. One well known irrigating device is a simple bulb syringe, which syringe may include check valves. The bulb syringe is filled from a basin containing the desired sterile liquid to be employed for washing or irrigating in cleaning the wound. The bulb syringe has serious disadvantages' in that (1) it must be filled repeatedly during use from a basin which has the sterile liquid exposed to the atmosphere of the surroundings (2) it contains a small liquid volume and (3) can be dropped easily during use. Improvements have been proposed to the simple disposable bulb syringe in its being combined with a reservoir containing the sterile liquid to be used for washing and cleaning the wound. Various types of combinations of a bulb syringe and a liquid reservoir or vessel have been proposed. None of these improved devices has found full acceptance by the medical profession because of various problems with them. The improved syringes, although manually operable, do not allow the user to initiate gently and direct positively any desired liquid volume and stream intensity into the wound. It is difficult to design one syringe arrangement which is easy to control by hand operation of a desired stream volume and intensity.

Many syringe devices have been used for irrigating wounds because they could be made for one use and disposal of inexpensive and easily formed plastic materials, sterilized and then retained in such sterile form until ready to use. However, electric, pneumatic or hydraulic driven pumping systems have been designed where the user may activate, as for example by a push button or the like, a hand held nozzle assembly to control the delivery of a pressurized stream of sterile liquid onto the wound. These devices are very expensive to manufacture and use. They are difficult to clean after use so that they may be returned into a sterile condition for the next usage. In many cases, the medical profession has preferred the disposable, hand held simple syringe and a basin containing liquid for cleaning wounds with a washing liquid.

The present invention is a medical irrigation device, which combines the ready to use and inexpensive disposable features of the simple bulb syringe with the great utility in delivery of volumes of sterile fluids provided by the motor driven irrigating devices of the more sophisticated nature discussed above. In particular the present medical irrigating device is of a very unique design, constructed of plastic components that are inexpensive to fabricate and assemble, and further capable of providing selectively the desired liquid volume and intensity of stream from a hand held syringe but yet without the undesired features of the simple plastic bulb syringe and basin arrangement. In addition, this new medical irrigation device can be readily maintained sterile within its wrappings until desired to be used when it is filled with the sterile liquid to be used in cleaning the wound. Then, the device is ready to use by simple manual manipulations of hand held syringes. In addition, this device can be used with a plurality of syringes by several medical professionals where the washing of the wound requires a relatively large volume of carefully directed and controlled washing liquid streams.

SUMMARY OF THE INVENTION

In accordance with this invention there is provided a medical irrigation device for one time use and disposal where a selected volume and stream intensity in liquid flow is provided by simple manual manipulation. The device has a tubular base with a flat resting surface. An inverted transparent reservoir vessel with a closed top and open bottom is mounted fluid tight to the base and sealed at its open bottom with a closure member. Several hand operated syringes are connected to the vessel by flexible hoses which extend from fluid outlets beneath the closure member and outwardly from the base.

In the preferred embodiment, the syringe has a tubular body with a liquid outlet tapered nozzle at one end and a removable squeeze bulb at its other end. A liquid inlet is positioned in the body between a spring loaded outlet check valve near the nozzle and the squeeze bulb. An inlet check valve is mounted in the body at the inlet. The syringe is so arranged that regulated compression of the squeeze bulbs initiates the liquid stream in volume and intensity, as desired, from the nozzle. However, the syringe can rest dribble free between uses.

In other embodiments, the device is arranged to be readily constructed from molded plastic parts which are readily assembled through a simple mechanical arrangement into a device having the simplicity and economy of simple bulb syringes but yet capable of producing the volume and stream intensity of the much more complex power driven irrigating devices used in surgical procedures.

DESCRIPTION OF THE DRAWINGS

In these drawings, the several embodiments of the device have common elements of construction. In regards to the several figures, like elements carry like numerals to simplify the description of these embodi-

DESCRIPTION OF PREFERRED EMBODIMENTS

Figure 1:
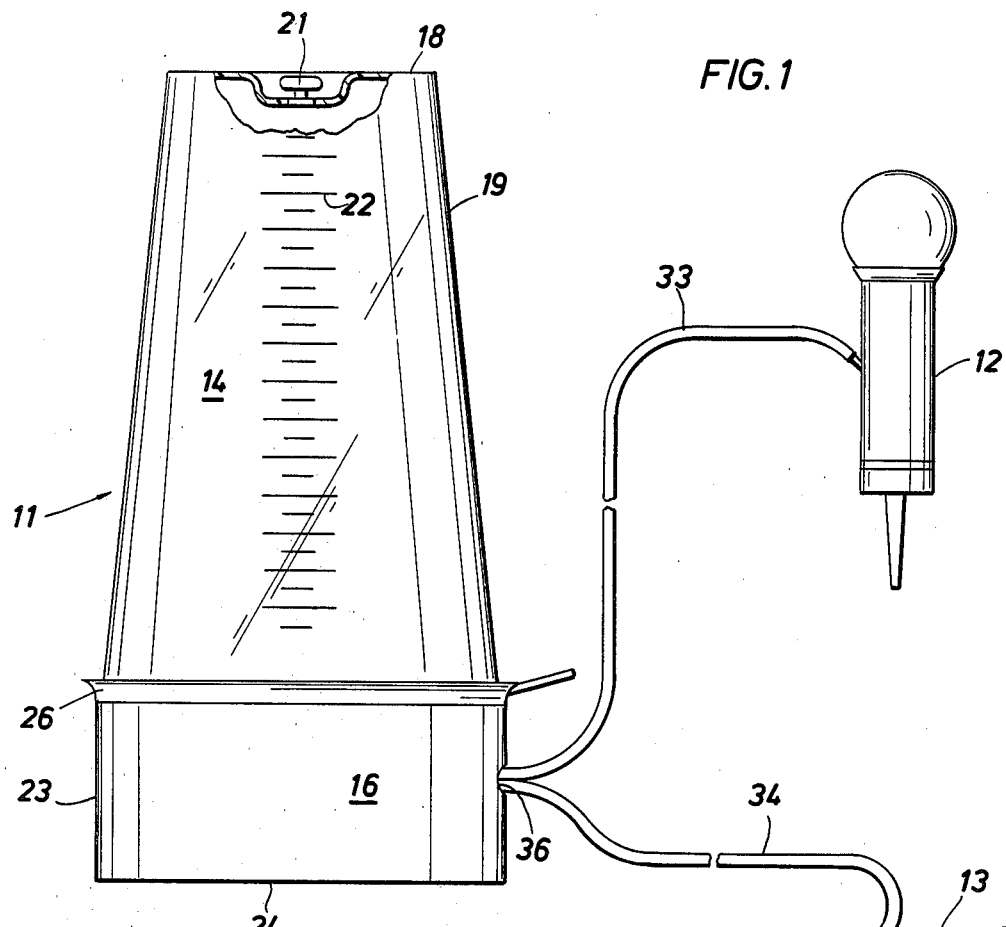
FIG. 1 is a pictorial view illustrating one embodiment of the medical irrigating device which is arranged with two hand operated syringes in accordance with the present invention.
Figure 7:
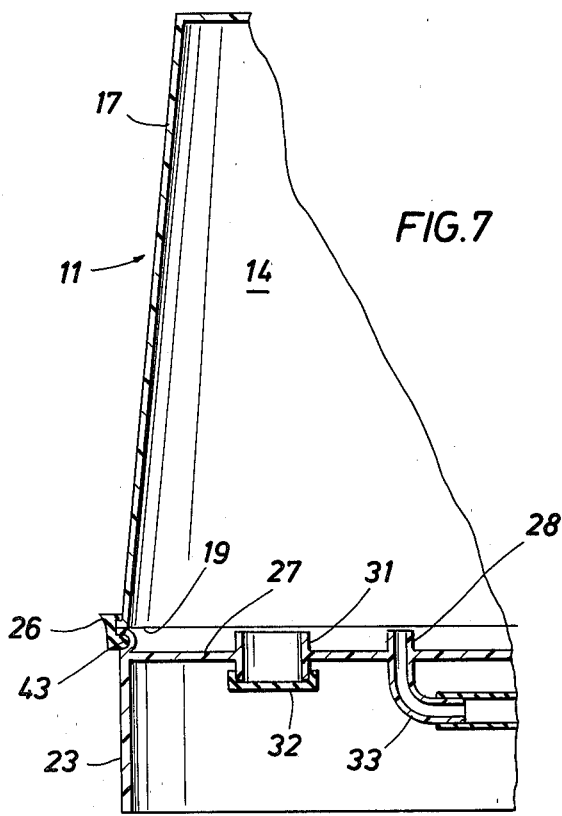
FIG. 7 is a partial vertical section taken through the device shown in FIG. 1.

Referring to FIG. 1, there is shown a medical irrigation device which is constructed in accordance with the present invention. In this particular device 11, there are two syringes 12 and 13 which are adapted to direct separately or simultaneously streams of wash liquid held within a reservoir 14 mounted upon a base 16. The center of gravity of the device is near the upright axis of the base and the device therefore resists tipping is use. More particularly, the reservoir 14 is provided by a transparent vessel 17 which preferably is formed in an inverted conical shape. The vessel 17 has a closed top 18 and an open bottom 19 (which is shown in FIG. 7). The top 18 carries a push-to-open vent valve 21 so that a gas vent is provided to prevent a vapor lock of the sterile liquid which is contained in the reservoir 14. The reservoir 14 may be provided with volumetric calibrating marks 22 so that the amount of wash liquid in the reservoir 14 can be determined at a glance by the user of the syringes. The valve 21 should be so arranged as to be below the upper surface of the top 18 so that when the device 11 is inverted, the valve is not accidentally opened.

The vessel 17 is mounted to a tubular base 23 that has a wide stance flat bottom surface 24 to rest upon a suitable table support next to the operating table where it is used for providing liquid flow for cleaning wounds or other surgical irrigation. The vessel 17 is secured to the base 23 by a resilient annular gasket 26 which will be described in more detail hereinafter.

Figure 5:
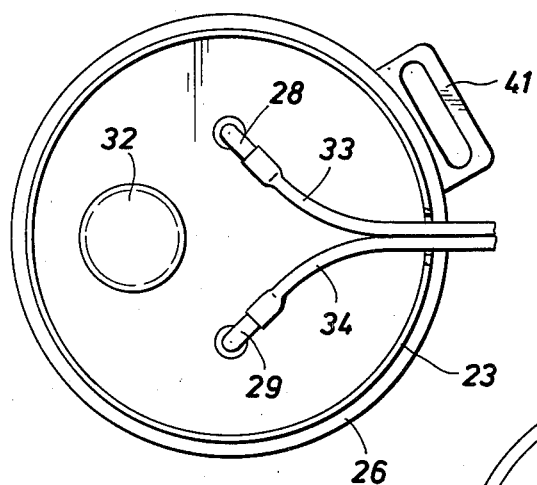
FIG. 5 is a bottom view of the device shown in FIG. 1.

Referring momentarily to FIGS. 5 and 7, the base 23 carries a flat closure member 27 that seals the open bottom 19 of the vessel 17 to the base 23 by action of the gasket 26. The closure member 27 carries outlet tubes 28 and 29 that are integrally molded into the member 27. In addition, the cover member 27 carries an integral inlet port 31 which can be covered with a snap fastening closure 32. It will be apparent with the device 11 inverted, that the cover 32 is removed from the port 31. Then, the reservoir is 14 filled with sterile liquid through the port 31. Lastly, the cap 32 is snapped back into place over the port 31 and the device 11 can be set upright upon its base 23.

The outlet tubes 28 and 29 are connected by flexible hoses 33 and 34 which pass through the base 23 by an opening 36 to interconnect with the syringes 12 and 13, respectively. Usually, these hoses will be of a length of approximately 3 feet which has been found to be of convenient length for allowing the syringes to be moved about the patient and used with great facility.

Figure 8:
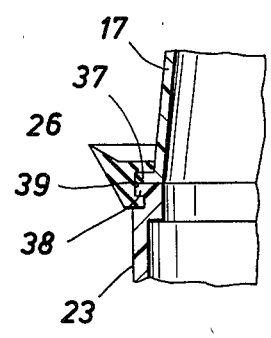
FIG. 8 is an enlarged partial section of the structure shown in FIG. 7 illustrating the gasket interconnecting the reservoir vessel with the base.

The vessel 11 and the base 23 are arranged so as to readily interconnected by the gasket 26. Referring to FIG. 8, the vessel 17 has an outwardly extending flange 37 whereas the base 23 has a complimentary outwardly extending flange 38. These flanges are secured together within a groove 39 in the gasket 26. The lower edge of the gasket rests in an annular groove 43 in the sidewall of the base 23. Preferably, the gasket 26 is molded from a resilient polysulfane polymer material, so that it is readily placed into position with the groove 39 embracing the flanges 37 and 38 in fluid tightness. Other means of securing the vessel to the base may be employed, if desired.

Figure 6:
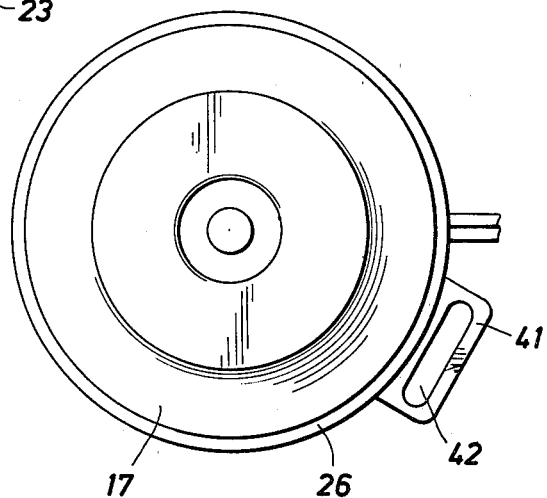
FIG. 6 is a plan view of the device shown in FIG. 1.

As can be seen in the several FIGS. 1, 5 and 6, the gasket 26 preferably has an outwardly extending lip 41 which may include a gripping ear 41 with an opening 42 to assist in placing or removing the gasket about the flanges carried upon the vessel and the base. A tool may be placed through the opening 42 to facilitate the final mounting of the gasket with its groove embracing the flanges 37 and 38.

Figure 2:
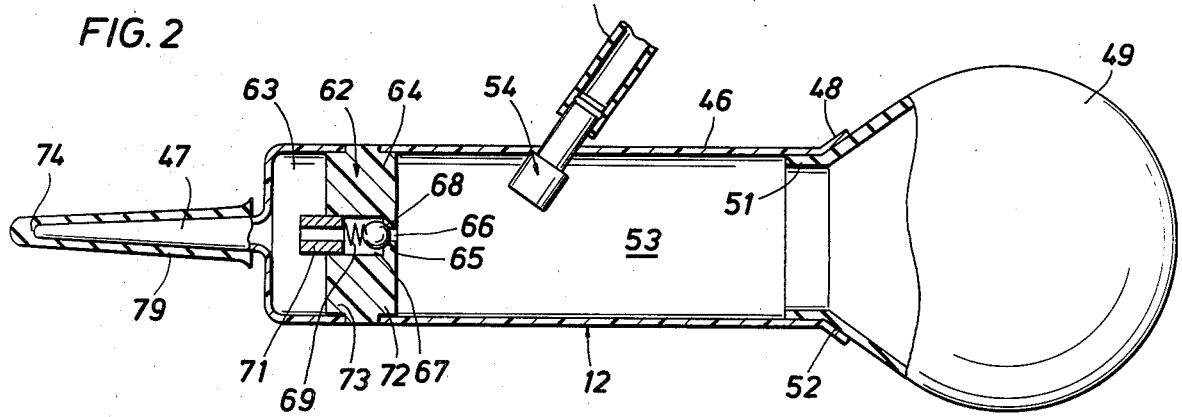
FIG. 2 is a partial longitudinal sectional view of one of the syringes shown in FIG. 1.
Figure 4:
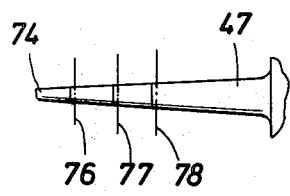
FIG. 4 is a partial view of the nozzle of the syringe in FIG. 2 with dash lines showing the ready shearing of the nozzle tip to provide varying stream intensities from the syringe.
Figure 3:
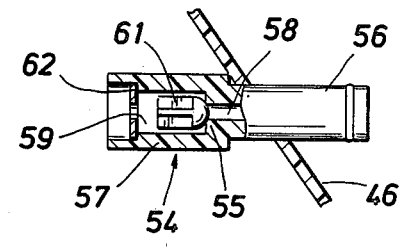
FIG. 3 is a partial longitudinal section of the inlet check valve employed in the syringe shown in FIG. 2.

The unique construction of the syringes can be appreciated in more detail by referring to the FIGS. 2, 3 and 4. Since the syringes are identical in this particular embodiment of the medical irrigating device 11, only the syringe 12 will be described in detail. The syringe 12 has a tubular body 46 with a coaxial liquid outlet tapered nozzle 47 carried at one end of the body. The other end of the body carries a flared lip or flange 48 in which is mounted a removable squeeze bulb 49. More particularly, the bulb 49 has a tubular mouth 51 which is received into the body for a short distance internally of the flared lip 48. The curved surface 52 of the bulb 49 cooperates with the lip 48 for providing an inward seat and to assist in holding the bulb 49 in fluid tight mounting within the body 46. If desired, the bulb 49 can be pulled slightly from the body 46 to provide a downstream vent for permitting the internal compartment 53 of the syringe 12 to be liquid filled by gravity flow through the hose 33 from the reservoir 11. The hose 33 connects to the chamber 53 by an inlet check valve 54 which is integrally secured in the body 46 by adhesives or heat sealing of thermoplastic materials.

The inlet check valve 54 is shown in greater detail in FIG. 3. More particularly, the check valve 54 has an inlet port 56 which penetrates through the sidewall of the body 46. Within the body's chamber 53, the check valve 54 has a body 57 with an inlet 58 connecting the nozzle port 56 to an enlarged chamber 59 in which there is carried a free floating poppet valve 61. The valve 61 is retained by a holding ring 62 to prevent its loss from the check valve into the chamber 53. The check valve 54 is so arranged that the valve 61 is substantially free floating within the sterile liquid entering the syringe 12 through the hose 33. As a result, any return movement of the liquid from the chamber 53 into the hose 33 causes the valve 61 to immediately seat against the shoulder 55 provided by the reduced diameter port 58. However, since the valve is free floating, it moves readily into its open position to permit fluid to pass from the hose 33 into the chamber 53 by gravity or through the action of releasing a partially collapsed squeeze bulb 49.

In addition, the body 46 carries an outlet check valve assembly 62 that is mounted adjacent the nozzle 47. Preferably, the outlet chamber 63 downstream of the check valve 62 is only a very small proportion in volume to the capacity of the chamber 53. If desired, the outlet chamber 63 may be only the void of the nozzle 47. For this result, the nozzle 47 can be secured directly to the outlet check valve 62. This relatively small volumetric chamber 63 is an important feature in that it permits a more delicate control of the volume and stream intensity obtained by squeezing the bulb 49. It also prevents a dribbling of a large volume of liquid from the nozzle 47 if the outlet valve 62 should leak. More particularly, the valve assembly 62 is formed with a cylindrical body 64 which has an inlet port 66 opening into an enlarged valve chamber 67. Within the chamber 67 is mounted a ball check valve member 68 which is held against the port 66 by a spring 69. The spring is secured within the chamber 67 by a tubular outlet port member 71 which may be secured within the body 64 by heat sealing or an adhesive. The member 71 could be formed as part of the nozzle 47. If desired, the several portions of the body can be secured to shoulders 72 and 73 formed in the body 64 by a suitable adhesive or other integrally connecting arrangement.

Preferably, the spring 69 provides a delicate but definite bias to seat the ball 68 against the shoulder 65 formed by the port 66 in the body 64. As a result, fluid can not dribble from the nozzle 47 when the syringe 12 is not in use as when it is laying upon a tray next to an operating table.

Preferably, the inlet check valve 54 is tipped at an angle rearwardly towards the bulb 49 which makes for easily handling of the syringe 12. It will be apparent that with the described arrangement of the syringe 12 that the syringe is readily aimed by grasping the bulb 49 between the thumb and the first two fingers. A very delicate control squeezing of the bulb by the fingers can be readily obtained. There is a natural aiming tendancy for the syringe 12 when it is held between these fingers. As a result a very slight compression of the bulb 49 causes an immediate stream of liquid to be discharged from the nozzle 47 and the intensity and volume of the stream is readily regulated by the amount of force exerted by the fingers in compressing the bulb 49.

The syringe 12 has another novel feature in design of the nozzle 47. The nozzle 47 is molded preferably from a very soft nonfrangible plastic, so that it may be readily trimmed adjacent its sealed tip 74 as can be seen in FIG. 4. For example, the nozzle 47 may be trimmed at a selected several positions indicated by dash lines 76, 77 or 78 so that the nozzle opening can be of a selected size. This produces the desired dimension in the stream of liquid discharged from the syringe 12. If desired, the tip of the nozzle 47 may be closed before use or during use by a tapered nozzle cover 79 which is held by a simple friction fit upon the nozzle 47.

Although it will be apparent that the present medical irrigation device 11 can be constructed from a variety of materials, it is preferred that the vessel 17 be formed by injection molding from a transparent acrylic plastic material. The opening to receive the push to open valve 21 may be formed at the same time during its molding, and likewise, the graduations 22 can be provided by suitable indicia carried in the mold. The base 23 can be provided of a soft nonfrangible plastic material such as polypropyolene. The gasket 26 can be molded of a suitable soft but resilient plastic such as polysulfone or polyethylene resilient polymers. The hoses 33 and 34 can be formed of any suitable flexible hose material, and Teflon plastic is a suitable material. As to the syringes, preferably their bodies 46 are molded from a transparent acrylic plastic that can be heat, or adhesive (or sealed). The check valves 54 and 62 are preferably formed from Teflon materials so as to be completely chemical resistant and dimensionally stable. Obviously, the nozzle 47 can be integrally molded with the liquid outlet portion of the body 46. The squeeze bulb 49 is preferably molded from a soft but resilient plastic material such as a synthetic rubber or the like. Other materials for preparing the device 11 by molding or otherwise forming them can be used, if desired.

From the foregoing, it will be apparent that there has been provided a novel medical irrigation device which is readily constructed from plastics by molding and assembled by simple mechanical techniques. The device after assembly can be sterilized by suitable well known techniques, such as by injecting ethylene oxide and then sealing it in a plastic film pack. When it is desired to employ the device, the plastic film pack is removed from the device 11 and the reservoir 14 filled with the desired sterile solution. Then, the syringes are lowered and the bulb 49 may be slightly released so that chambers 53 will fill with liquid through gravity flow effects. If not, with the nozzle 47 severed to open it to the atmosphere, the squeeze bulb 49 may be depressed several times to aspirate liquid from the reservoir 14 and fill the chamber 53. Now, the syringe 12 is ready to use in washing wounds in the surgical irrigation procedures.

It will be appreciated that certain changes or alterations in the construction of the present medical irrigating device may be made without departing from the spirit of this invention. These changes are contemplated by and are within the scope of the appending claims which define the present invention. Additionally, the present description is intended to be taken as an illustration of this invention.

What is claimed is:

1. A medical irrigation device of one use and disposal design for providing manually selective volume and stream intensity in liquid flow, the device comprising:
    (a) a tubular base having a flat resting surface;
    (b) an inverted transparent reservoir vessel with a closed top and open bottom;
    (c) mounting means holding in fluid tight engagement said reservoir vessel onto said base and sealing the open bottom of said reservoir with a closure member;
    (d) outlet conduit means carried in said closure member and extending downwardly within said base;
    (e) at least one hand operated syringe;
    (f) a flexible hose interconnecting an inlet on said syringe with said outlet conduit means;
    (g) and said flexible hose extending from said base adjacent said closure member whereby the device resists tipping even when empty of liquid.

2. The device of claim 1 wherein said syringe has a tubular body, a liquid outlet tapered nozzle at one end of said body, a removable squeeze bulb at the other end of said body and said inlet positioned in said body between a spring loaded outlet check valve adjacent said nozzle and said squeeze bulb, and an inlet check valve mounted in said body at said inlet.

3. The device of claim 2 wherein said inlet is angularly tipped towards said squeeze bulb.

4. The device of claim 2 wherein said inlet check valve introduces liquid into a chamber including said squeeze bulb, which chamber is several fold larger in volume than the liquid path between said outlet check valve and said nozzle.

5. The device of claim 4 wherein said squeeze bulb has a tubular open mouth received within a flared open end on said body whereby said syringe can be primed substantially void free with liquid from said vessel while in a subtended position by sliding said mouth on said squeeze bulb from said flared open end on said body.

6. The device of claim 2 wherein said tapered nozzle is formed of soft and non-frangible plastic which is readily trimmed selectively to a nozzle opening for providing a desired stream size.

7. The device of claim 1 wherein said vessel is provided with an inlet port covered by a removable closure disposed in said closure member whereby the device is inverted and readily filled with a liquid through said inlet port.

8. The device of claim 1 wherein said vessel is provided with a vent valve carried in its closed top, and said vent valve is opened when delivery of liquid is desired from said syringe.

9. The device of claim 1 wherein said vessel at its open end carries an outward flare and said base carries a complementary outward flare, and said mounting means includes an annular resilient gasket with an internal groove receiving and securing in fluid tight interconnection said outward flares of said vessel and said base.

10. The device of claim 1 wherein on said syringe said inlet check valve is of the type having a free moving valve member and said outlet check valve is lightly spring biased into the closed position whereby a slight compression of said squeeze bulb initiates a liquid stream from said nozzle but said syringe can rest dribble free when resting on a supporting work surface.

* * * * *